United States Patent [19]

Loshaek et al.

[11] Patent Number: 5,491,091
[45] Date of Patent: Feb. 13, 1996

[54] CONTACT LENS DISINFECTING SYSTEM

[75] Inventors: Samuel Loshaek, Chicago, Ill.; Helmut Singer, Pittsford, N.Y.

[73] Assignee: Schering Corporation, Kenilworth, N.J.

[21] Appl. No.: 809,551

[22] PCT Filed: Jul. 31, 1990

[86] PCT No.: PCT/US90/04194

§ 371 Date: Jan. 28, 1992

§ 102(e) Date: Jan. 28, 1992

[87] PCT Pub. No.: WO91/01763

PCT Pub. Date: Feb. 6, 1991

[51] Int. Cl.⁶ .............................................. A61L 2/16
[52] U.S. Cl. .................... 436/1; 422/28; 422/30; 252/95; 252/188.27; 252/187.26
[58] Field of Search .................. 436/1; 422/28, 422/30; 206/5.1; 252/106, 95, 188.27, 186.26

[56] References Cited

U.S. PATENT DOCUMENTS

| | | | |
|---|---|---|---|
| 4,265,847 | 5/1981 | Hunt et al. | 264/122 |
| 4,414,127 | 11/1983 | Fu | 252/95 |
| 4,670,178 | 6/1987 | Huth et al. | 252/95 |
| 4,826,658 | 5/1989 | Kay | 422/30 |
| 4,863,627 | 9/1989 | Davies et al. | 252/95 |
| 5,035,859 | 7/1991 | Gu et al. | 422/28 |

FOREIGN PATENT DOCUMENTS

| | | | |
|---|---|---|---|
| 978852 | 12/1975 | Canada | 167/2 |
| 0147100 | 7/1985 | European Pat. Off. | G02C 13/00 |
| 2134666 | 12/1972 | France | A61L 13/00 |
| 0199170 | 7/1985 | Netherlands | A61K 53/04 |
| 1221038 | 2/1971 | United Kingdom | A61J 3/10 |
| 2144875 | 3/1985 | United Kingdom | A61L 2/00 |
| 8605695 | 10/1986 | WIPO | A61L 2/18 |

OTHER PUBLICATIONS

Janoff, The Optician, Aug. 1979, pp. 28–30.

*Primary Examiner*—Lyle A. Alexander
*Attorney, Agent, or Firm*—Warrick E. Lee, Jr.

[57] ABSTRACT

A method is disclosed for disinfecting contact lenses with peroxide whereby the usual peroxide neutralization step is eliminated. This is accomplished by carrying out the disinfecting process at a hydrogen peroxide concentration of about 0.01 to less than 0.5% (w/v). In the preferred embodiment the peroxide is introduced into the system utilizing an effervescent tablet of an alkali metal perborate, percarbonate or persulfate, or urea peroxide.

5 Claims, No Drawings

5,491,091

CONTACT LENS DISINFECTING SYSTEM

FIELD OF INVENTION

This invention relates to a system for disinfecting contact lenses. In particular it relates to a method for disinfecting contact lenses utilizing a solid source of peroxide at dilute concentrations which obviates the need for a neutralization step.

BACKGROUND OF THE INVENTION

Contact lenses require frequent cleaning in order to remove deposits, the source of which is generally tear fluid. In addition to cleaning it is necessary to disinfect contact lenses to reduce the risk of infection. A common method of disinfecting contact lenses is to contact them with a three percent solution of hydrogen peroxide.

Prior art methods of disinfecting first clean and rinse the lenses and then immerse them in an aqueous three percent solution of hydrogen peroxide for about 20 minutes. The lens is then treated to reduce the residual hydrogen peroxide absorbed therein to a level which is non toxic and non irritating to the eye. In the prior art residual hydrogen peroxide has been reduced chemically by immersing the lens in an aqueous neutralizing solution followed by rinsing with isotonic saline. While neutralization has been accomplished in numerous ways in the prior art, one approach is to place the lenses in a container of saline solution having a plastic disc coated with catalytic platinum for about 4 hours. Other methods for neutralizing peroxide included immersion of the lens in an aqueous isotonic saline containing catalase or thiosulfate, or bisulfite and pyruvate salts and the like.

Another prior art method to reduce the residual peroxide employs multiple rinses and soaking with isotonic saline due to the high concentration (3%) of the peroxide employed in the disinfection step. Bausch and Lomb Quick Sept disinfection solution is of this type.

British patent number 2,144,875A (British '875) discloses a process for the oxidative cleansing of contact lenses which is similar to that utilized in cleansing dentures. An oxidative cleansing solution is prepared using a solid material which gives chemical release of hydrogen peroxide. Illustrative examples of solid materials giving chemical release of hydrogen peroxide include percarbonates, persulfates, perborates, peroxyhydrates and other per salts of alkali metals and other anions.

U.S. Pat. No. 4,414,127 discloses a method of utilizing a transition metal catalyzed peroxide solution to cleanse contact lenses. The preferred metal is copper.

U.S. Pat. No. 4,670,178 discloses a composition for simultaneously cleaning and disinfecting contact lenses which comprises a peroxide and a peroxide stable proteolytic enzyme. The peroxide concentration is such that the microbial load is reduced by one log order in three hours. At the lower end, this level is disclosed to be about 0.5% weight/volume peroxide. While there is no upper limit to peroxide concentration except as limited by the requirement that the enzyme retains proteolytic activity, the preferred range is about 1 to 2% (w/v) peroxide. Most preferably a solution of about 3% to about 10% (w/v) hydrogen peroxide is used. Although concentrations of peroxide as low as 0.02% (w/v) are disclosed and claimed, at those low levels the peroxide is disclosed as an activator for the enzyme and not as a disinfectant. The peroxide source can be hydrogen peroxide and its metal salts, alkali metal perborate monohydrate and tetrahydrate, alkali metal persulphates, alkali metal percarbonate peroxides, diperisophthalic acid, peroxydiphosphate salts and sodium aluminum aminohydroperoxide. The need to degrade unreacted peroxide is disclosed as part of the disinfecting/cleansing operation, A lens disinfecting system available in Europe comprises a two solution system. The first solution for disinfecting the lens comprises 0.6% (w/v) of hydrogen peroxide together with cleaning additives. The second solution comprises a catalyst for deactivating residual peroxide. After treating the lens with the peroxide solution for a time to disinfect it, the lens is then soaked in the second solution for a time sufficient to deactivate residual peroxide.

SUMMARY OF THE INVENTION

This invention is predicated on the surprising discovery that aqueous solutions of peroxide in a specific concentration range are capable of performing disinfection, yet neutralizing after disinfection is not required.

This invention may be summarized as a process for disinfecting a contact lens comprising contacting the lens with an aqueous liquid containing hydrogen peroxide at a concentration of about 0.01 to less than 0.5% weight/volume (more preferably about 0.05 to about 0.2% (w/v)) for a time sufficient to disinfect the lens followed by wearing the lens without neutralizing residual peroxide. Preferably the aqueous liquid containing hydrogen peroxide is formed by dissolving a solid source of peroxide in a predetermined amount of aqueous liquid. The solid peroxide source is preferably a perborate, a percarbonate, a persulfate, a peroxyhydrate or urea peroxide, and more preferably it is sodium perborate monohydrate or urea peroxide. The solid peroxide source is preferably in a unit dose in powder or tablet form, also containing an organic acid and a solid carbonate or bicarbonate.

DETAILED DESCRIPTION OF THE INVENTION

This invention relates to a method for disinfecting contact lenses which obviates the need for neutralizing unreacted peroxide or removing unreacted peroxide by multiple rinses as is generally a requirement of prior an methods. It is conventional and preferred in contact lens care regimens to rinse the lens after cleaning and after disinfecting just prior to insertion in the eye to insure removal of foreign matter from the lens surface. This last rinse may further reduce traces of residual peroxide on the lens surface and inasmuch as it is a conventional step, this invention contemplates using a conventional rinse as the preferred method of use but also includes use without a rinse step following disinfection. This result is achieved by utilizing a low level of peroxide which is sufficient to adequately disinfect the lens while at the same time not leaving an amount of unreacted peroxide which would require a chemical neutralization step to make the contact lens safe for application to the eye. There may be a small minority of contact lens wearers who may be especially sensitive to minute amounts of peroxides or other chemicals, but this invention satisifies the needs of the large majority of wearers. In its preferred embodiment the peroxide source is a water soluble solid peroxide. The term "solid peroxide" as used in the specification and claims in intended to mean a chemical compound which, when dissolved in water, releases hydrogen peroxide.

Illustrative, non-limiting examples of solid peroxides suitable for use in the practice of this invention are alkali metal perborate monohydrate and tetrahydrate, alkali metal persulfates, alkali metal percarbonate peroxides, urea peroxides, diperisophthalic acid, peroxydiphosphate salts and sodium aluminum aminohydroperoxide.

The inventive compositions are adapted to be mixed with a quantity of aqueous liquid to form contact lens disinfecting solutions having specific concentrations of hydrogen peroxide. A preferred way to adapt the composition for use is to supply the solid peroxide in a unit dosage form, e.g. tablets or envelopes containing a unit dose of the composition in powdered form.

In carrying out the method of this invention, a predetermined amount of solid peroxide is added to a measured amount of aqueous liquid so that the hydrogen peroxide concentration in solution is about 0.01 to less than 0.5% weight/volume. The amount of solid peroxide required to achieve such a range of hydrogen peroxide is readily calculated by those skilled in the art. The type of peroxide selected will determine the amount of solid peroxide required. By way of example, if the solid peroxide is sodium perborate monohydrate, the desired hydrogen peroxide concentration (0.01 to less than 0.5%) is achieved by utilizing about 0.29 mg. to about 14 mg. of solid peroxide per milliliter of aqueous liquid. Preferably, the peroxide concentration in solution is about 0.05 to about 0.2% (w/v). To the said solution in the container the contact lens is added, capped and stored for a time sufficient to disinfect the lens. It is immaterial which component of the system is added first. After disinfection by any process, it has become common practice to rinse off the lenses, just prior to insertion in the eye to insure removal of any foreign matter. As noted above this rinsing step is preferred but not required.

If desired, various excipients can be added to the peroxide/water system including salts, buffers and stabilizers so that the disinfecting solution will have the proper pH and tonic value. Additionally, cleansing agents to aid in cleansing the lens can be included. Illustrative, non-limiting examples of such cleansing agents are sodium lauryl sulfate, alkyl aryl polyether alcohols, monocarboxylated, dicarboxylated or sulphonated fatty acid substituted imadazoline surfactants and EDTA. Optionally, a tonicity salt may be included in the composition.

In its preferred embodiment the peroxide is prepared in an effervescent powder to tablet form. Effervescence is achieved by incorporating into the composition a solid acid and a solid carbonate source which, when reacted with the solid acid in solution, generates carbon dioxide. Illustrative, non-limiting, examples of solid carbonate sources are sodium carbonate and sodium bicarbonate. Illustrative, non-limiting, examples of solid acids suitable for use in the practice of this invention are inorganic monosodium phosphate and organic acids such as adipic acid, glutaric acid, and anhydrous citric acid. Where the solid peroxide is in tablet form, it is preferred that a lubricant and/or tabletting aid be included in the composition. The use of adipic acid or glutaric acid obviates the need for a lubricant in the tabletting process. Suitable tabletting aids include polyethylene glycol waxes, stearic acid and alkali metal stearates.

The tablet size or quantity of powdered solid peroxide source will depend entirely on the quantity of liquid to be used. A convenient tablet size containing the proper amount of active ingredients is about 4 to about 50 mg. of active ingredient (solid peroxide). Preferably about 10 to about 45 mg. of active ingredient are used. The amount of active ingredient used fixes the range of the quantity of aqueous liquid used since the active hydrogen peroxide concentration in solution must be less than 0.5% (w/v); preferably about 0.05 to about 0.2% (w/v). The aqueous liquid may comprise as little as one milliliter or as much as 15 ml. The amount of liquid is not critical. It is, however, preferred that sufficient liquid is utilized to totally immerse the lens in the liquid to insure contact of the lens with the solution which is preferably agitated by the gas generated by the effervescent mixture.

Before disinfecting with the composition of this invention, it is preferable to clean the lens by one of the many commercial methods.

As noted, a major advantage of the inventive system is the elimination of a chemical neutralization step and, therefore, elimination of a burdensome neutralizing component. In addition this provides greater convenience to the user making compliance to the regimen simpler and more likely.

Another advantage of this invention is that various aqueous liquids for dissolving the solid peroxide composition can be utilized. The aqueous liquid can be any clean liquid which is predominantly water, and which contains no ingredients which will harm the lens or interfere with the disinfection process. The aqueous liquid can be ordinary tap water, preserved saline solution, sterile saline solution, deionized water, distilled water or mixtures thereof so long as the liquid does not contain any component which could inhibit the disinfection reaction.

Yet another advantage is that the pH of the disinfection system of this invention can be matched to that of the eye when the solid disinfectant is added to the liquid. This is unlike the 3% hydrogen peroxide systems which require a pH of 3–4 for stabilization. Exposure of many commercial lenses of this pH can cause undesirable dimensional changes.

Another advantage of the invention is that various excipients can be included in the tablet, such as salts, buffers and stabilizers, which when dissolved in the aqueous liquid will have the proper neutral pH and tonic values. The conventional 3 percent hydrogen peroxide systems must be maintained at acid pH in the range of 3.5–4 in order to prevent decomposition of the peroxide in storage. This acidic pH level is known to be a cause of eye irritation. Since the disinfecting tablet is stored in the dry condition, there is no need for acidic conditions to prevent premature decomposition and in fact it is desirable for the tablet to contain a basic salt such as carbonates or bicarbonates to produce a substantially neutral solution or slightly basic pH when added to the liquid.

In one aspect of the invention the method for disinfecting contact lenses comprises the steps of:

(1) Immersing a contact lens in a liquid comprising water or a saline solution having a peroxide concentration of about 0.01 to less than 0.5 percent (w/v) hydrogen peroxide for a time sufficient to disinfect the lens. The liquid being free of peroxide reducing agents; and (2) wearing the lens on the eye without subjecting the lens to a peroxide reducing agent.

It is common practice and highly recommended by eye care practitioners to rinse lenses after immersion in any disinfectant medium. While the present invention does not require a rinsing step to reduce residual peroxide, it is likely that such a step would be employed. However, the step of reducing residual hydrogen peroxide, so critical to prior art methods utilizing higher concentrations of hydrogen peroxide, is not necessary when using the method of this invention. Thus inadvertent or purposeful omission of the rinsing step is not harmful.

Any suitable container may be utilized to carry out the disinfecting process of this invention. Many such containers have been used in commerce. Said containers are made of clear or opaque plastic and include a mark or the like thereon to indicate a specific volume of aqueous liquid, and a cover for the container. The container may be made to contain a single contact lens in which case two containers are used to disinfect a pair of lenses. Alternatively commercial containers are available which hold two lenses so designed as to isolate the right and left lenses.

The following examples are intended to illustrate, but not limit, the invention.

EXAMPLE 1

GENERAL PROCEDURE

This Example illustrates the preferred method of using tablets of powders of the present invention to disinfect contact lenses, and describes a method for testing disinfecting efficacy. Except for the disinfection step using the inventive tablet, this procedure is typically used for the care of contact lenses.

A commercial contact lens carrying case for two lenses, which holds about 7.5 m. of liquid is filled with unpreserved saline or other aqueous liquid. Hydrophylic contact lenses are cleaned with a commercial contact lens cleaner such as PLIAGEL™, made by Wesley-Jessen or LC-65™, made by Allergan, by rubbing the lens between the thumb and index finger, and rinsing with saline solution, such as Weslery-Jessen's "Unisol Plus" unpreserved aerosol packaged saline solution. The choice of cleaner and rinse solution is not critical. The lenses are then placed in the carrying case containing 7.5 ml of aqueous liquid. A tablet or powder formulation of this invention is added. Effervescence and dissolution takes place in less than 5 minutes. After a time sufficient to disinfect the lens, the lens is removed from the case, rinsed with saline solution and inserted into the eye. A rinsing step is conventionally used and is preferred after disinfecting contact lenses to remove any possible foreign matter.

Disinfecting efficacy is tested according to FDA Guidelines. Briefly, micro organisms are added to a sterile test tube filled with saline solution to yield about $10^6$ Colony Forming Unites per milliliter (FCU/ml). The exact concentration of CFU per ml in the test tube is determined shortly before the disinfection formulation is added.

Thereafter, aliquots are withdrawn from the vial at desired time intervals in accordance with the Testing Guidelines. These methods were employed with the formulations of the following examples.

EXAMPLE 2

Tablets were prepared using the following formulations:

| | |
|---|---|
| Sodium Perborate Monohydrate (active ingredient) | 22.0 mg. |
| Sodium Carbonate[1] | 12.5 mg. |
| Adipic Acid[1] | 25.0 mg. |
| Carbowax @ 6000[2] | 1.2 mg. |

[1]Effervescent components
[2]Carbowax 6000 is solid polyethylene glycol manufactured by Dow Chemical Company and is a lubricating substance to aid in tablet forming.

1—Effervescent components

2—Carbowax 6000 is solid polyethylene glycol manufactured by Dow Chemical Company and is a lubricating substance to aid in tablet forming.

EFFICACY TESTS

The antimicrobial activity of the above formulation was tested against various micro-organisms as required by the Testing Guidelines for Class III Soft Contact Lens Solutions, issued by the U.S. Food and Drug Administration, Jul. 15, 1985. A tablet of the above formulation was used in 7.5 ml. of sterile saline solution. The results are shown in Table I.

TABLE I

| D-Values[1] in Minutes | |
|---|---|
| ORGANISM | D-Value (Min.)[2] |
| S. marcesens | 76 |
| Ps. aeruginosa | <2 |
| S. epidermidis | <2 |
| A. Niger | 50 |

[1]D-Value is the time required to reduce a microbial challenge by 90% or one logarithm.
[2]Values reported in FDA Tech. Report 6095-8905-008 "D-Value Determination"

The above data show that by exposing a contact lens to the method of this invention the lens will be disinfected substantially in less than two hours, while some organisms will be removed in the order of minutes.

EXAMPLE 3

Compositions shown in the table below were prepared in tablet or powder form. The procedure for testing disinfecting efficacy of Example 2 was followed. The column labeled wt %/v $H_2O_2$ represents the concentrations of hydrogen peroxide that is generated upon dissolution of the peroxide releasing component in 7.5 ml of aqueous liquid, the capacity of the contact lens carrying case which holds two lenses.

EXAMPLE 3A

| Ingredients | mg | wt %/v of $H_2O_2$ in Solution |
|---|---|---|
| Sodium perborate monohydrate | 44 | 0.20 |
| Sodium bicarbonate | 15 | |
| Citric acid | 23 | |
| Time: | 0 Min. | 120 Min. |
| Log CFU/ml of C. albicans: | 5.7 | <1 |

EXAMPLE 3B

| Ingredients | mg | wt %/v of $H_2O_2$ in Solution |
|---|---|---|
| Sodium perborate monohydrate | 11 | 0.05 |
| Sodium bicarbonate | 15 | |
| Citric acid | 8.5 | |
| Time: | 0 Min. | 240 Min. |
| Log CFU/ml of C. albicans: | 5.1 | <1 |

EXAMPLE 3C

| Ingredients | mg | Approx. wt %/v of $H_2O_2$ in Solution |
|---|---|---|
| Sodium Perborate monohydrate | 22 | 0.10 |
| Sodium bicarbonate | 20 | |
| Citric acid | 10 | |
| Triton X-100[a] | 0.75 | |
| Time: | 0 Min. | 180 Min. |
| Log CFU/ml of *C. albicans*: | 4.8 | <1 |

[a]Triton X-100 is a non-ionic detergent manufactured by Rohm & Haas.

EXAMPLE 3D

| Ingredients | mg | Approx. wt %/v of $H_2O_2$ in Solution |
|---|---|---|
| Sodium perborate monohydrate | 5.5 | 0.25 |
| Urea peroxide | 50.0 | |
| Sodium carbonate | 5.5 | |
| Adipic acid | 12.2 | |
| Time: | 0 Min. | 240 Min |
| Log CFU/ml of *C. albicans*: | 5.9 | 3.0 |
| *A. niger* | 5.1 | <1 |

EXAMPLE 3E

| Ingredients | mg | Approx. wt %/v of $H_2O_2$ in Solution |
|---|---|---|
| Sodium perborate monohydrate | 5.5 | 0.15 |
| Urea peroxide | 26.0 | |
| Sodium carbonate | 5.5 | |
| Adipic acid | 12.2 | |
| Triton X-100 | 0.75 | |
| Time: | 0 Min. | 240 Min. |
| Log CFU/ml of *C. albicans*: | 5.0 | 2.7 |
| *A. niger*: | 5.0 | <1 |

EXAMPLE 3F

| Ingredients | mg | Approx. wt %/v of $H_2O_2$ in Solution |
|---|---|---|
| Urea peroxide | 44 | 0.20 |
| Sodium carbonate | 7 | |
| Adipic acid | 14 | |
| Time: | 0 Min. | 240 Min. |
| Log CFU/ml of *C. albicans*: | 5.5 | <1 |

What is claimed is:

1. A process for disinfecting a contact lens comprising:
   (a) providing a fixed quantity of aqueous liquid;
   (b) dissolving a unit dose of a solid composition in the aqueous liquid to form a disinfecting solution, said unit dose comprising:
      (1) sufficient solid peroxide source to cause the disinfecting solution to have a concentration of 0.01 to less than 0.5 percent weight/volume hydrogen peroxide.
      (2) solid carbonate or bicarbonate, and
      (3) organic acid;
   (c) contacting the lens with the disinfecting solution at room temperature for a time sufficient to disinfect the lens; and
   (d) wearing the lens without neutralizing residual peroxide.

2. The process of claim 1 wherein the concentration of hydrogen peroxide in the disinfecting solution is from 0.05 to 0.2 percent weight/volume.

3. The process of claim 2 wherein the organic acid is adipic acid.

4. The process of claim 3 wherein the solid unit dose further comprises:
   (4) polyethylene glycol.

5. The process of claim 4 wherein the solid unit dose is in tablet form.

* * * * *